United States Patent
Censo et al.

(10) Patent No.: US 9,414,964 B2
(45) Date of Patent: Aug. 16, 2016

(54) EARPLUG FOR SELECTIVELY PROVIDING SOUND TO A USER

(71) Applicant: HARMAN INTERNATIONAL INDUSTRIES, INC., Stamford, CT (US)

(72) Inventors: Davide Di Censo, San Mateo, CA (US); Stefan Marti, Oakland, CA (US)

(73) Assignee: Harman International Industries, Inc., Stamford, CT (US)

( * ) Notice: Subject to any disclaimer, the term of this patent is extended or adjusted under 35 U.S.C. 154(b) by 196 days.

(21) Appl. No.: 14/147,445

(22) Filed: Jan. 3, 2014

(65) Prior Publication Data

US 2015/0190284 A1    Jul. 9, 2015

(51) Int. Cl.

| | |
|---|---|
| *G10K 11/16* | (2006.01) |
| *A61F 11/08* | (2006.01) |
| *H04R 1/10* | (2006.01) |
| *G10K 11/175* | (2006.01) |
| *A61F 11/14* | (2006.01) |

(52) U.S. Cl.
CPC .............. *A61F 11/08* (2013.01); *G10K 11/175* (2013.01); *H04R 1/1016* (2013.01); *H04R 1/1083* (2013.01); *A61F 2011/145* (2013.01); *G10K 2210/108* (2013.01); *G10K 2210/1081* (2013.01); *H04R 1/1041* (2013.01); *H04R 2460/01* (2013.01)

(58) Field of Classification Search
CPC ................ G10K 2210/1081; G10K 2210/108; G01H 3/14; H04R 29/00
USPC ..................................... 381/56, 71.1, 71.6, 74
See application file for complete search history.

(56) References Cited

U.S. PATENT DOCUMENTS

| | | |
|---|---|---|
| 5,027,410 A | 6/1991 | Williamson et al. |
| 6,989,744 B2 * | 1/2006 | Proebsting ............... 340/539.15 |
| 7,512,247 B1 | 3/2009 | Odinak et al. |
| 8,081,780 B2 * | 12/2011 | Goldstein et al. ............. 381/119 |

(Continued)

FOREIGN PATENT DOCUMENTS

WO    2008103295 A1    8/2008

OTHER PUBLICATIONS

Mueller et al., "Transparent Hearing," (CHI 2002), http://floydmueller.com/projects/transparent_hearing/, 1 page.

(Continued)

*Primary Examiner* — Disler Paul
(74) *Attorney, Agent, or Firm* — Artegis Law Group, LLP

(57) ABSTRACT

One embodiment of the present invention sets forth an earplug for selectively providing sound to a user. The earplug includes a microphone, a processing unit, and a speaker. The microphone is configured to acquire ambient sound. The processing unit is configured to determine that a first sound included in the ambient sound is associated with a first set of sound parameters and, in response, generate a first cancellation signal associated with the first sound. The processing unit is further configured to determine that a second sound included in the ambient sound is associated with a second set of sound parameters and, in response, generate a second signal to cause the second sound to be produced. The speaker is configured to produce one or more sound waves based on the first cancellation signal to cancel the first sound from the ambient sound and produce the second sound based on the second signal.

22 Claims, 7 Drawing Sheets

(56) References Cited

U.S. PATENT DOCUMENTS

| | | | |
|---|---|---|---|
| 2003/0235313 A1* | 12/2003 | Kurzweil | A61F 11/12 381/71.6 |
| 2005/0036637 A1 | 2/2005 | Janssen | |
| 2005/0226425 A1 | 10/2005 | Polk, Jr. | |
| 2008/0267416 A1* | 10/2008 | Goldstein | H04R 1/1091 381/56 |
| 2010/0076793 A1 | 3/2010 | Goldstein et al. | |
| 2011/0069843 A1* | 3/2011 | Cohen | H04S 1/00 381/56 |
| 2011/0107216 A1 | 5/2011 | Bi | |
| 2012/0215519 A1 | 8/2012 | Park et al. | |
| 2013/0273967 A1 | 10/2013 | Dave et al. | |
| 2015/0071457 A1* | 3/2015 | Burciu | H04R 1/1016 381/74 |

OTHER PUBLICATIONS

Basu et al., "Smart Headphones," Proceedings of CHI 2001, Seattle, WA, pp. 267-268, http://alumni.media.mit.edu/~sbasu/papers/chi2001.pdf.

European Search Report for EP 14 19 9731, dated May 27, 2015.

International Search Report and Written Opinion for PCT/US2015/010234 dated Apr. 29, 2015.

Non-Final Office Action dated Dec. 9, 2015 for U.S. Appl. No. 14/148,689.

* cited by examiner

| Sound | Configuration A | Configuration B | Configuration C |
|---|---|---|---|
| Baby | Pass | Pass | Pass |
| Alarm | Pass | Enhance | In-ear |
| Partner's Alarm | Block | Block | Block |
| Snoring | Block | Block | Block |
| Other Sounds | Pass | Pass | Pass |

FIG. 4

EARPLUG FOR SELECTIVELY PROVIDING SOUND TO A USER

BACKGROUND

1. Field of the Embodiments of the Invention

Embodiments of the present invention generally relate to signal processing and, more specifically, to an earplug for selectively providing sound to a user.

2. Description of the Related Art

Sleep plays an important role in maintaining healthy brain function, physical health, and overall well-being. As a result, people commonly go to great lengths to improve the quality of their sleep, such as by taking medications and supplements, undergoing sleep studies, and carefully controlling the environment in which they sleep. Even so, many people continue to suffer from sleep disruptions.

One common sleep disruption is caused by auditory distractions in the surrounding environment that prevent a person from falling asleep or wake the person from sleep. Such distractions may include, for example, talking, snoring, music playing, vehicles, and other noises in the surrounding environment. In an attempt to prevent such distractions from disrupting sleep, many people have turned to devices such as "white" noise machines, which attempt to mask potentially disruptive noises with a continuous hissing sound. While some find the sound generated by white noise machines soothing, others find it distracting. However, in either case, the sound generated by white noise machines typically is not loud enough to mask sounds that are very loud and/or very close to the user, such as the snoring of the user's partner.

Another common technique for attempting to prevent auditory distractions from disrupting sleep is the use of earplugs. Earplugs are inserted into the user's ear canals and, to varying degrees, block sounds in the surrounding environment. As such, earplugs are generally effective at preventing auditory distractions from disrupting the user's sleep. However, because earplugs block all sounds in the surrounding environment, the user is unable to hear useful and/or important sounds, such as an alarm clock, a baby crying, a fire alarm, and the like. Consequently, due to the risks associated with missing these types of sounds in the surrounding environment, the use of earplugs is impractical for many people.

As the foregoing illustrates, techniques that enable a user to more effectively prevent auditory distractions in the surrounding environment from disrupting the user's sleep would be useful.

SUMMARY

One embodiment of the present invention sets forth an earplug for selectively providing sound to a user. The earplug includes a microphone, a processing unit, and a speaker. The microphone is configured to acquire ambient sound. The processing unit is configured to determine that a first sound included in the ambient sound is associated with a first set of sound parameters and, in response, generate a first cancellation signal associated with the first sound. The processing unit is further configured to determine that a second sound included in the ambient sound is associated with a second set of sound parameters and, in response, generate a second signal to cause the second sound to be produced. The speaker is configured to produce one or more sound waves based on the first cancellation signal to cancel the first sound from the ambient sound and produce the second sound based on the second signal.

Further embodiments provide, among other things, a method and a non-transitory computer-readable medium configured to the earplug set forth above.

Advantageously, the disclosed technique enables the user to selectively block sounds in the surrounding environment. Additionally, the user is able to specify which sounds are passed through the earplugs and/or enhanced by the earplugs, further increasing the likelihood that the user will not miss useful and/or important sounds in the surrounding environment. Further, the disclosed techniques enable the user to transmit an alarm signal directly to the earplugs such that the user's alarm does not disturb people nearby the user.

BRIEF DESCRIPTION OF THE SEVERAL VIEWS OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 4 illustrates different configurations for blocking, passing, and enhancing sounds via the earplug of FIGS. 1A and 1B, according to various embodiments of the present invention;

DETAILED DESCRIPTION

In the following description, numerous specific details are set forth to provide a more thorough understanding of the embodiments of the present invention. However, it will be apparent to one of skill in the art that the embodiments of the present invention may be practiced without one or more of these specific details.

Figure 1A:
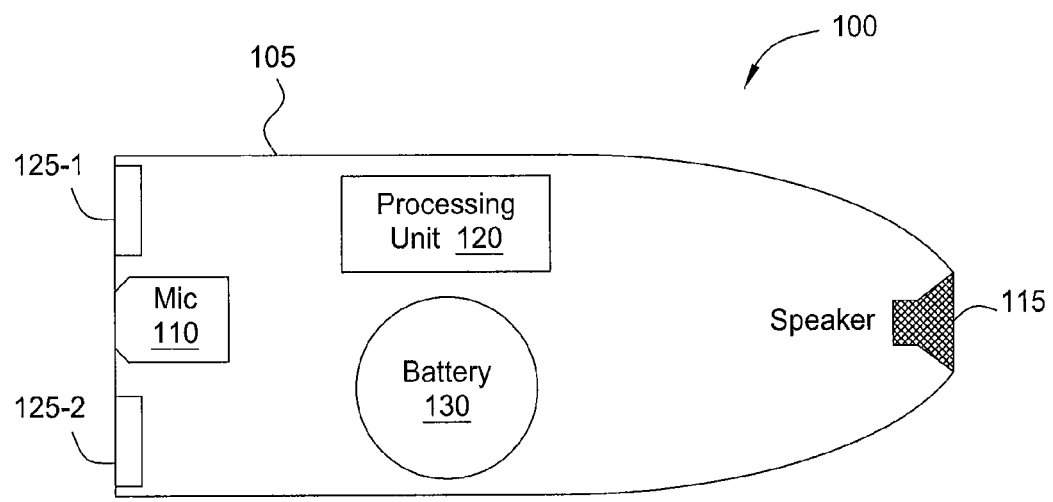
FIGS. 1A and 1B illustrate an earplug for selectively providing sound to a user, according to various embodiments of the present invention.
Figure 1B:
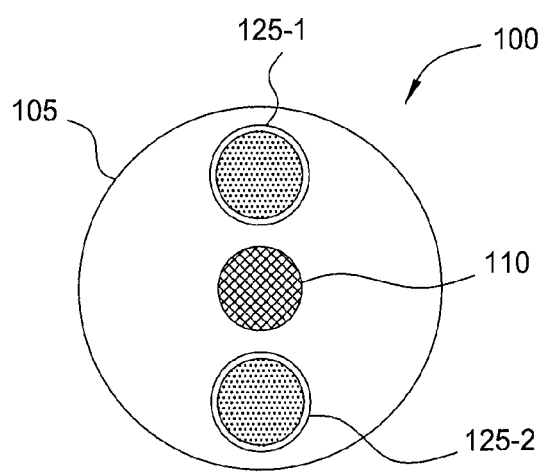

FIGS. 1A and 1B illustrate an earplug for selectively providing sound to a user, according to various embodiments of the present invention. The earplug 100 may include, without limitation, an earplug body 105, a microphone 110, a speaker 115, a processing unit 120, one or more input devices 125 (e.g., input device 125-1 and input device 125-2), and a battery 130. The earplug body 105 may include a flexible material, such as a polymer, foam, silicone, rubber, etc., that conforms to a user's ear canal and provides some degree of isolation from noises in the surrounding environment. The earplug body 105 may be shaped to fit the ear canal of a variety of different users, or the earplug body 105 may be shaped to fit the ear canal of a specific user, such as by custom molding the earplug body 105 to the user's ear canal. In other embodiments, the earplug body 105 may include a non-flexible material, such as hard plastic or metal, and/or may not provide substantial isolation from noise in the surrounding environment.

The microphone 110 is configured to acquire sound from the surrounding environment and transmit signals associated with the sound to the processing unit 120. As such, the microphone 110 may be located in a portion of the earplug body 105 that faces outward, away from the user, when the earplug body 105 is inserted into the ear canal. Alternatively, the microphone 110 may be physically separate from the earplug body 105 and coupled to the earplug 100 via a wired connection or wireless connection. For example, in order to more effectively acquire sound from the surrounding environment, the microphone 110 may be positioned proximate to the user's outer ear and coupled to the earplug 100 via a wired connection or wireless connection.

The speaker 115 may be located in a portion of the earplug body 105 that faces inward, towards the user's ear canal. The speaker 115 is configured to produce sounds based on signals that are generated by the processing unit 120 and/or other signals that are transmitted to the speaker 115. For example, the speaker 115 may be configured to produce ambient sounds that are acquired by the microphone 110, processed by the processing unit 120, and transmitted to the speaker 115. In some embodiments, the speaker 115 is configured for high-fidelity sound reproduction. In other embodiments, in order to reduce the size and/or cost of the speaker 115, the speaker 115 may be configured for less accurate sound reproduction. For example, in some embodiments, the speaker 115 may be configured to produce only a subset of frequencies within the normal human hearing range.

The processing unit 120 is configured to receive signals from the microphone 110, process the signals, and transmit the processed signals to the speaker 115. The processing performed by the processing unit 120 may include, for example, filtering, amplification, attenuation, and/or other types of auditory enhancements.

In various embodiments, the processing unit 120 may be configured to block or permit certain sounds acquired by the microphone 110. For example, the processing unit 120 may analyze signals received from the microphone 110 to determine whether one or more sounds acquired by the microphone 110 substantially match a set of sound parameters. The set of sound parameters may include, for example, one or more frequencies ranges, loudness values, digital signatures, and/or other characteristics that enable the processing unit 120 to identify a particular sound acquired by the microphone 110. If one or more signals received from the microphone 110 match a set of sound parameters, then the processing unit 120 may process the signal(s) to block, pass-through, or enhance the sounds with which the signals are associated.

In some embodiments, the set(s) of sound parameters may be stored in a memory associated with the earplug 100. The memory may include one or more databases, such as a blocked sounds database and a permitted sounds database. In such embodiments, if one or more signals received from the microphone 110 substantially match a set of sound parameters stored in the blocked sounds database, then the processing unit 120 may process the signal(s) to block the sounds with which the signals are associated. Sounds may be blocked, for example, via active noise cancellation, passive noise isolation (e.g., provided by the earplug body 105), and/or merely by not reproducing the sounds for the user via the speaker 115.

If one or more signals received from the microphone 110 substantially match a set of sound parameters stored in the permitted sounds database, then the processing unit 120 may process the signal(s) to permit the sounds with which the signals are associated. The processing unit 120 may permit sounds by transmitting signals to the speaker 115 to cause the sounds to be produced by the speaker 115. Sounds may be produced by the speaker 115 with substantially the same auditory characteristics (e.g., loudness, pitch, tempo, frequency range, etc.) at which they were acquired by the microphone 110. That is, the sounds may be passed-through from the microphone 110 to the speaker 115 via the processing unit 120. In addition, the processing unit 120 may permit sounds by enhancing the sounds, such as by modifying one or more auditory characteristics of the sounds, and producing the sounds for the user. For example, the processing unit 120 may increase the loudness of a sound (e.g., relative to the loudness at which the sound was acquired by the microphone 110) and transmit a signal to the speaker 115 to cause the speaker 115 to produce the sound at the increased loudness value.

The processing unit 120 may perform noise cancellation by analyzing the signals received from the microphone 110 and generating one or more cancellation signals. The cancellation signals are then transmitted to the speaker 115 and produced in order to cancel one or more sounds in the surrounding environment. For example, the processing unit 120 may determine that a signal received from the microphone 110 substantially matches a set of sound parameters included in the blocked sounds database. In response, the processing unit 120 may generate one or more cancellation signals (e.g., inverted phase signals) and transmit the cancellation signal(s) to the speaker 115. The speaker 115 may then produce the cancellation signal(s) in order to block one or more sounds in the surrounding environment.

In some embodiments, the microphone 110, speaker 115, processing unit 120 and/or battery 130 may be included in a system-on-chip (SoC) configuration. Such embodiments may enable components of the earplug 100 to be more efficiently manufactured. Additionally, including some or all of these components on a single substrate and/or die may improve power efficiency and enable the size of the earplug 100 to be reduced. The battery 130 may include a rechargeable battery or a one-time-use battery, such as a battery that is "printed" onto a substrate included in the earplug 100. Additionally, the battery 130 may be removable or non-removable from the earplug 100.

In various embodiments, the input devices 125 may include one or more buttons, switches, knobs, keypads, etc., configured to activate one or more functions of the earplug 100. The functions may include, for example, a selective pass-through function, a selective enhancement function, a noise cancellation function, a learning function, and an alarm function. For example, during operation of the earplug 100, a user may operate an input device 125, such as the first button 125-1 and/or second button 125-2 shown in FIGS. 1A and 1B, to select the selective pass-through function. When the selective pass-through function is selected, the earplug 100 may be configured to acquire ambient sound with the microphone 110 and pass-through only sounds that are associated with one or more sets of sound parameters stored in the permitted sounds database. Other sounds, such as sounds that are associated with a set of sound parameters stored in the blocked sounds database, are not passed-through to the user.

When the selective enhancement function is selected, the earplug 100 may be configured to acquire ambient sound with the microphone 110 and determine which sounds, if any, are associated with one or more sets of sound parameters stored in the permitted sounds database. Sounds that are associated with a set of sound parameters stored in the permitted sounds database may then be passed-through to the user, as described above, or enhanced by the processing unit 120 prior to being produced by the speaker 115. For example, if an entry in the permitted sounds database indicates that a sound associated with a particular set of sound parameters should be enhanced—instead of merely passed-through to the user—then the processing unit 120 may process the corresponding signals received from the microphone 110 to enhance one or more auditory characteristics (e.g., loudness, frequency range, pitch, etc.) of the sound. The sound is then produced by the speaker 115 according to the enhanced auditory characteristics. Other sounds, such as sounds that are associated with a set of sound parameters stored in the blocked sounds database, are not enhanced by the processing unit 120. In some embodiments, when the earplug 100 is performing the selective enhancement function, sounds that do not substantially match a set of sound parameters in the permitted sounds database or the blocked sounds database are passed-through to the user by default. In other embodiments, the selective enhancement function blocks all sounds that do not substantially match a set of sound parameters in the permitted sounds database.

When the noise cancellation function is selected, the earplug 100 may be configured to acquire ambient sound with the microphone 110 and determine which sounds, if any, are associated with a set of sound parameters stored in the blocked sounds database. Active noise cancellation may then be performed to block sounds that are associated with a set of sound parameters stored in the blocked sounds database, as described above. For example, if, during operation of the earplug 100, the processing unit 120 determines that a sound acquired by the microphone 110 matches a set of parameters associated with snoring, then the processing unit 120 may generate one or more cancellation signals and transmit the cancellation signal(s) to the speaker 115 to cancel out the snoring sound. Additionally, while the earplug 100 is performing the noise cancellation function, the processing unit 120 may also be configured to pass-through or enhance sounds that substantially match a set of sound parameters stored in the permitted sounds database. That is, the earplug 100 may be configured to perform noise cancellation while also performing sound pass-through and sound enhancement. Further, while the earplug 100 is performing the noise cancellation function, the processing unit 120 may be configured to pass-through all sounds that do not substantially match a set of sound parameters stored in the blocked sounds database.

When the learning function is selected, the earplug 100 may be configured to learn which sound(s) should be blocked (e.g., via noise cancellation) and which sound(s) should be permitted (e.g., via pass-through or enhancement). As such, the learning function may include a block function and a permit function. In some embodiments, one input device 125 (e.g., input device 125-1) is configured to activate the block function, while another input device 125 (e.g., input device 125-2) is configured to activate the permit function. In other embodiments, a single input device 125 (e.g., input device 125-1) is configured to activate both the block function and the permit function. For example, the user may input a long key press via the input device 125 to activate the block function and may input one or more short key presses via the input device 125 to activate the permit function. In still other embodiments, other numbers of input devices 125 and/or other key press methods of activating a particular function may be implemented.

When the block function is selected, the processing unit 120 analyzes signals received from the microphone 110 and generates one or more sets of sound parameters based on the signals. The processing unit 120 then stores the set(s) of sounds parameters in the blocked sounds database. For example, if a user wishes to teach the earplug 100 to block a snoring sound, the user may activate the block function and allow the microphone 110 to acquire the snoring sound. The processing unit 120 then analyzes the snoring sound, generates one or more sets of sound parameters associated with the snoring sound, and stores the set(s) of sound parameters in the blocked sounds database. Additionally, an entry in the blocked sounds database may indicate whether noise cancellation is to be performed with respect to a particular sound or whether the sound is to be blocked via passive noise isolation.

When the permit function is selected, the processing unit 120 analyzes signals received from the microphone 110 and generates one or more sets of sound parameters based on the signals. The processing unit 120 then stores the set(s) of sounds parameters in the permitted sounds database. For example, if a user wishes to teach the earplug 100 to permit an alarm clock sound, the user may activate the permit function and allow the microphone 110 to acquire the alarm clock sound. The processing unit 120 then analyzes the alarm clock sound, generates one or more sets of sound parameters associated with the alarm clock sound, and stores the set(s) of sound parameters in the permitted sounds database. In addition, the user may further specify (e.g., via an input device 125) whether the permitted sound is to be passed-through to the user or enhanced for the user.

When the alarm function is activated, the processing unit 120 may be configured to transmit an alarm signal to the speaker 115 to cause the speaker 115 to produce an alarm sound to alert and/or wake the user. In some embodiments, the alarm function may be configured to wake the user from sleep in a manner that is similar to a conventional alarm clock. However, in contrast to a conventional alarm clock, the alarm sound may be provided to the user such that other people nearby the user cannot hear the alarm sound. For example, as shown in Configuration C of FIG. 4, the alarm sound may be produced for the user in-ear (e.g., via the speaker 115) in order to wake the user, while the earplug body 105 provides passive noise isolation to substantially reduce or prevent the degree to which others near the user (e.g., the user's partner) can hear the alarm sound. In various embodiments, the alarm sound may be a conventional alarm sound, such as a beeping sound or a buzzer sound, or the alarm sound may be a spoken language alarm sound, such as a voice (e.g., a person whispering) that calmly wakes the user from sleep.

In addition to blocking, permitting, and/or enhancing sounds based on the learning functions described above, the earplug 100 may be configured (e.g., via software or firmware) to automatically pass-through or enhance certain sounds for the user. For example, when an important sound that may affect the safety of the user is detected, such as a fire alarm sound, a smoke detector sound, carbon monoxide alarm, etc., the earplug 100 may be configured to automatically pass-through or enhance the sound for the user regardless of whether the user has configured the earplug 100 to block or permit the important sound. The automatic pass-through and/or enhancement may be implemented using an "acoustic backdoor." Embodiments that enable automatic pass-through and/or enhancement may improve user safety and reduce manufacturer liability by ensuring that the earplug 100 does not block important sounds, for example, as a result of user error when the user operates the learning functions described above.

Figure 2A:
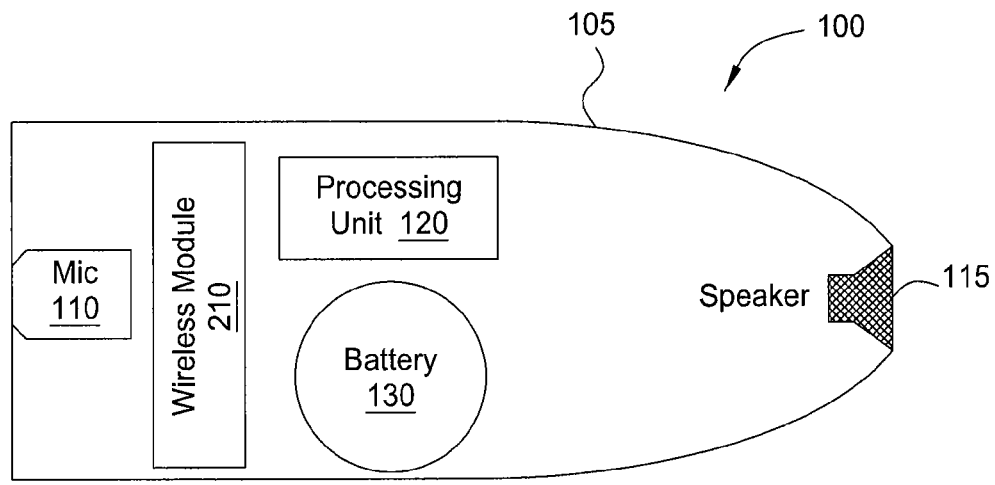
FIG. 2A illustrates the earplug of FIGS. 1A and 1B with an included wireless module, according to various embodiments of the present invention.
Figure 2B:
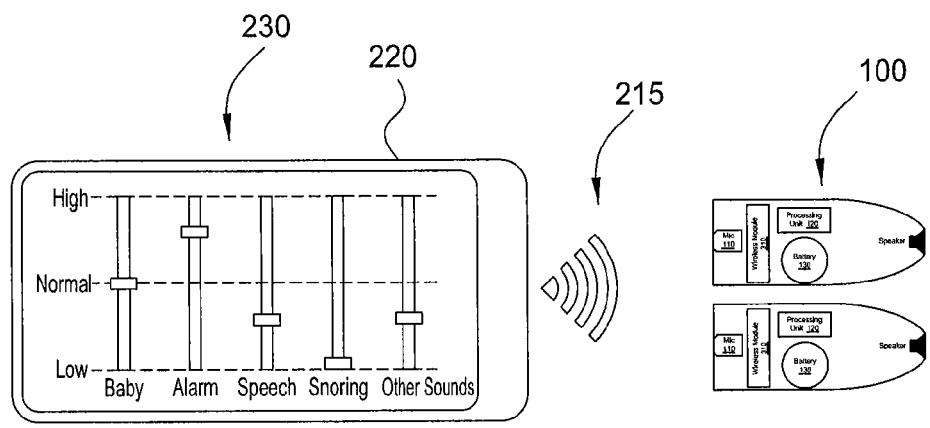
FIG. 2B illustrates a technique for transmitting sound parameters to the earplug of FIG. 2A, according to various embodiments of the present invention.

In some embodiments, the earplug 100 may be configured to transmit and/or receive information, such as one or more set(s) of sound parameters and/or an alarm signal, via a wireless connection 215. Accordingly, the earplug 100 may include a wireless module 210, as shown in FIG. 2A, which illustrates the earplug of FIGS. 1A and 1B with an included wireless module, according to various embodiments of the present invention. The wireless module 210 may be configured to transmit information to and/or receive information from an external computing device 220, enabling the user to configure the operation of the earplug 100 through an external interface. For example, the earplug may be configured wirelessly via a mobile computing device, such as a smartphone. Such an implementation is shown in FIG. 2B, which illustrates a technique for transmitting sound parameters to the earplug 100 of FIG. 2A, according to various embodiments of the present invention. The wireless module 210 may be a Bluetooth® module that transmits and/or receives information from an external computing device 220. In the same or other embodiments, the wireless module 310 may support any other wireless protocol including, for example, an 802.11 wireless standard, an optical communication standard (e.g., infrared communication), or any other radio frequency based standard. Additionally, the earplug 100 may be configured to transmit and/or receive the information described above via a wired connection, such as a universal serial bus (USB) interface, a proprietary wired connection, and the like.

In some embodiments, a user may create a set of sound parameters using an external computing device 220 and/or by downloading a set of sound parameters (e.g., via the Internet). For example, a user may access a preconfigured set of sound parameters that are associated with one or more common sounds (e.g., snoring sounds, baby sounds, various types of alarm sounds, and the like). The preconfigured set of sound parameters may then be transmitted to the earplug 100 (e.g., via a wired connection or wireless connection), enabling the user to specify which sounds are to be blocked or permitted without the need to activate and operate the learning function of the earplug 100.

Figure 3:
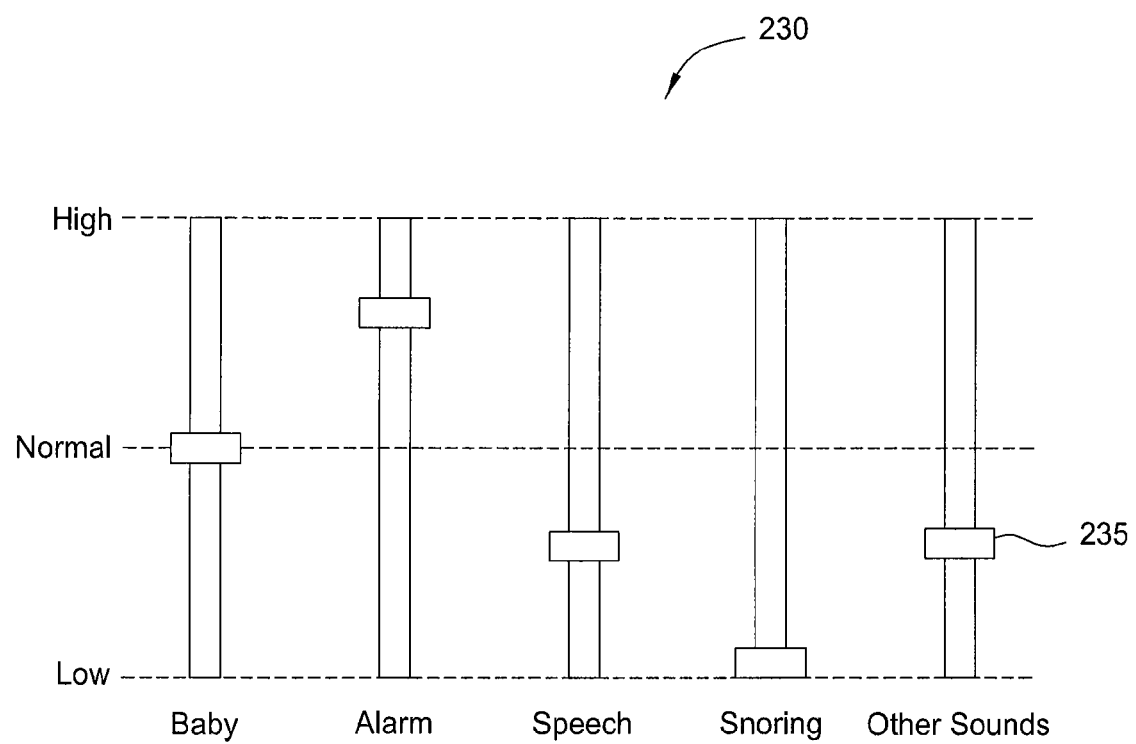
FIG. 3 illustrates a technique for specifying whether ambient sound is to be blocked, passed, or enhanced by the earplug of FIG. 2A, according to various embodiments of the present invention.

Operation of the earplug 100 may be configured via a user interface 230 provided by an external computing device 220, as shown in FIG. 3, which illustrates a technique for specifying whether ambient sound is to be blocked, passed, or enhanced by the earplug 100 of FIG. 2A, according to various embodiments of the present invention. In one implementation of the user interface 230, the user may manipulate one or more selectors 235 to specify how various sounds are to be processed by the processing unit 120 of the earplug 100. For example, a user may manipulate the selectors 235 to specify whether a particular sound is to be blocked or permitted and (optionally) how loud a permitted sound is to be produced by the speaker 115. The degree to which a particular sound is blocked or enhanced may be determined based on the location of a selector 235 on a continuum sound level values.

In some embodiments, sound level values may be specified as a percentage of the initial loudness of a particular sound. For example, a user may move a selector 235 to a percentage value of zero (e.g., corresponding to the 'Low' value in FIG. 3) when the user would like to attempt to completely block a particular sound. Further, the user may move a selector 235 to a percentage value of one-hundred (e.g., corresponding to the 'Normal' value in FIG. 3) when the user would like to pass-through a particular sound. In addition, the user may move a selector 235 to a percentage value above one-hundred (e.g., two-hundred percent) when the user would like to enhance a particular sound.

In other embodiments, the sound level values may include sound pressure levels (dBA SPL) and/or attenuation/gain values (e.g., specified in decibels). For example, a user may move a selector 235 to an attenuation value of −20 decibels (dB) (e.g., corresponding to the "Low" value in FIG. 3) when the user would like to attenuate a particular sound to one-fourth of the sound's initial loudness. Further, the user may move a selector 235 to a value of 0 dB (e.g., corresponding to the 'Normal' value in FIG. 3) when the user would like to pass-through a particular sound. In addition, the user may move a selector 235 towards a gain value of +20 dB (e.g., corresponding to the "High" value in FIG. 3) when the user would like to enhance a particular sound by increasing the loudness of the sound by up to four times the initial loudness. In the same or other embodiments, a user may specify the sound pressure level at which a particular sound is to be produced for the user. For example, the user may specify that the user's alarm is to be produced at 80 dBA SPL, while a partner's alarm clock is to be produced at 30 dBA SPL. In response, the processing unit 120 may increase the loudness of the user's alarm (e.g., from 60 dBA SPL to 80 dBA SPL) and reduce the loudness of the user's alarm (e.g., from 60 dBA SPL to 30 dBA SPL).

FIG. 4 illustrates different configurations for blocking, passing, and enhancing sounds via the earplug 100 of FIGS. 1A and 1B, according to various embodiments of the present invention. As shown, the selective pass-through function, selective enhancement function, and noise cancellation function, and alarm function described above may be implemented in different ways based on the hardware configuration of the earplug 100. For example, when the earplug 100 includes a single input device 125 (e.g., a single button), the earplug 100 may be configured to pass-through all sounds by default. The user may then specify each sound to be blocked (e.g., via active noise cancellation) by pressing the single input device 125 and allowing the microphone 110 to acquire the sound. Thus, as shown in Configuration A of FIG. 4, the block function of the earplug 100 may be activated by the user to teach the earplug 100 (e.g., via the microphone 110) to block a partner's alarm and a snoring sound. However, other sounds, such as a baby sound and the user's alarm, may be passed-through to the user by default.

In another embodiment, when the earplug 100 includes two input devices 125-1 and 125-2 (e.g., two buttons), the earplug 100 may be configured to pass-through all sounds by default. The user may then specify each sound to be blocked (e.g., via active noise cancellation) by pressing input device 125-1 (e.g., a first button) and allowing the microphone 110 to acquire the sound. Additionally, the user may specify each sound to be enhanced (e.g., via the selective enhancement function) by pressing input device 125-2 (e.g., a second button) and allowing the microphone 110 to acquire the sound. Thus, as shown in Configuration B of FIG. 4, the block function of the earplug 100 may be activated by the user to teach the earplug 100 to block a partner's alarm and a snoring sound, and the permit function may be activated by the user to teach the earplug 100 to enhance the user's alarm. However, other sounds, such as a baby sound, may be passed-through to the user by default.

In yet another embodiment, when the earplug 100 includes a wireless module 210, the earplug 100 may be configured to block or permit sounds in the surrounding environment based on one or more sets of sound parameters specified by the user via a graphical user interface (GUI) (e.g., user interface 230). When operating the GUI, the user may operate one or more selectors 235 to specify not only whether a particular sound is to be blocked, passed-through, or enhanced, but the degree to which blocking (e.g., via active noise cancellation) and/or enhancing (e.g., via amplification) are to be performed, as described above in conjunction with FIG. 3. That is, instead of merely indicating in a binary manner whether a particular sound is to be blocked or passed-through, the user may select from a continuum of values to fine tune the operation of the earplug 100. Additionally, the user may specify whether an alarm signal is to be transmitted to the earplug 100 to cause the earplug 100 to produce an alarm sound (e.g., an in-ear alarm sound). Thus, as shown in Configuration C of FIG. 4, the GUI may be operated by the user to specify whether a particular sound is to be blocked, passed-through, or enhanced, and whether an alarm sound is to be produced by the earplug 100.

Figure 5:
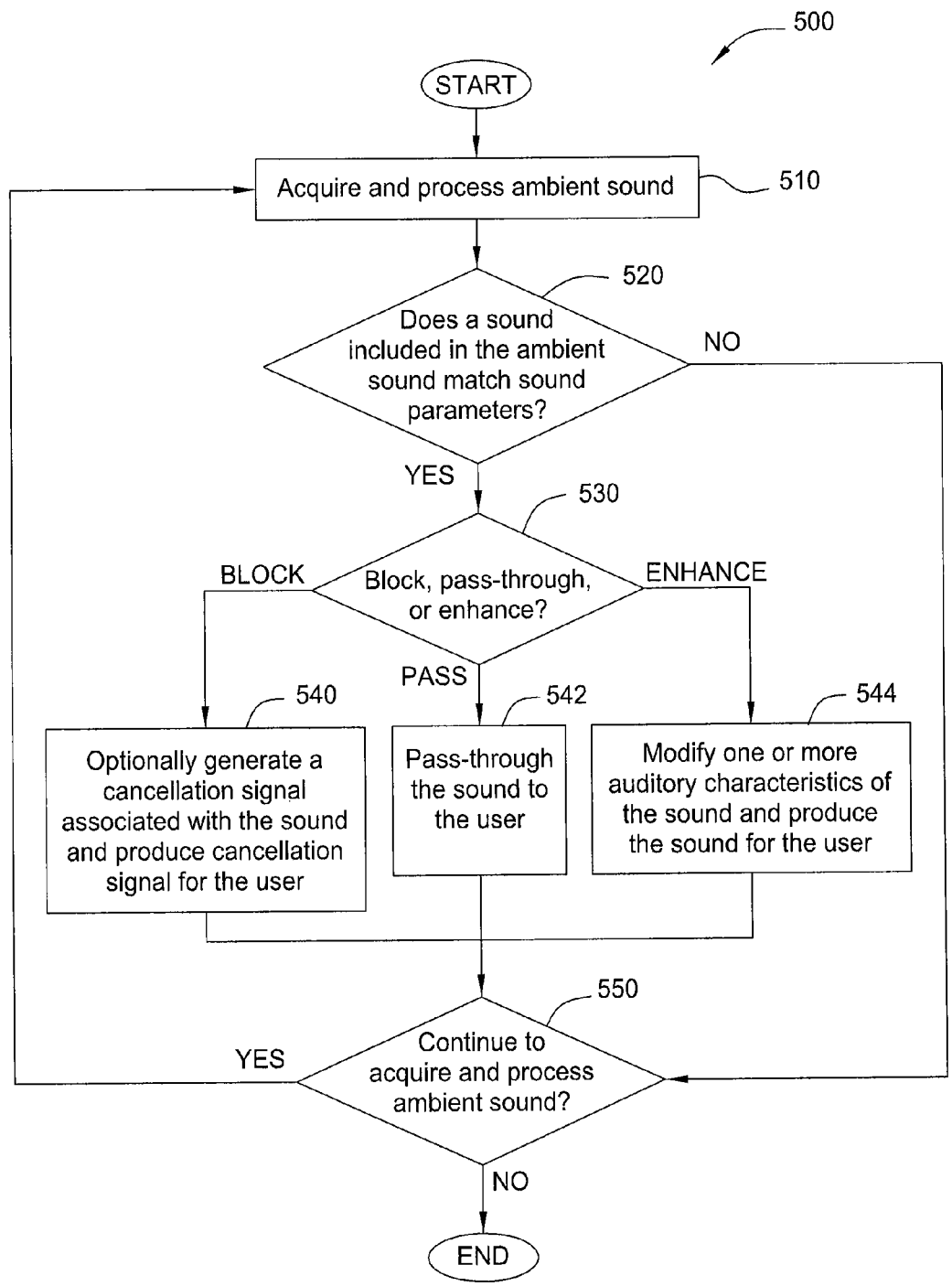
FIG. 5 is a flow diagram of method steps for selectively providing sound to a user via an earplug, according to various embodiments of the present invention.

FIG. 5 is a flow diagram of method steps for selectively providing sound to a user via an earplug, according to various embodiments of the present invention. Although the method steps are described in conjunction with the systems of FIGS. 1A-4, persons skilled in the art will understand that any system configured to perform the method steps, in any order, falls within the scope of the present invention.

As shown, a method 500 begins at step 510, where the microphone 110 acquires ambient sound and transmits signals associated with the ambient sound to the processing unit 120. The processing unit 120 then processes the signals associated with the ambient sound. At step 520, the processing unit 120 determines whether a sound included in the ambient sound substantially matches a set of sound parameters stored in the blocked sounds database or the permitted sounds database. If a sound included in the ambient sound substantially matches a set of sound parameters stored in the blocked sounds database or the permitted sounds database, then the method proceeds to step 530. At step 530, the processing unit 120 determines whether to block, pass-through, or enhance the sound. If the processing unit 120 determines that the sound should be blocked, then the method 500 proceeds to step 540, where the processing unit 120 may generate a cancellation signal associated with the sound. The processing unit 120 then transmits the cancellation signal to the speaker 115, which produces the cancellation signal to cancel the sound. Alternatively, instead of generating and producing a cancellation signal, the earplug 100 may block the sound merely by not producing the sound for the user. The method 500 then proceeds to step 550.

If, at step 530, the processing unit 120 determines that the sound should be passed-through, then the method 500 proceeds to step 542, where the processing unit 120 transmits one or more signals to the speaker 115 to cause the speaker 115 to produce the sound. The method 500 then proceeds to step 550. If, at step 530, the processing unit 120 determines that the sound should be enhanced, then the method 500 proceeds to step 544, where the processing unit 120 enhances the sound by modifying one or more auditory characteristics of the sound. The method 500 then proceeds to step 550.

In addition to determining whether to block, pass-through, or enhance a particular sound at step 530, the processing unit 120 may determine the degree to which the sound is to be blocked or enhanced. For example, the processing unit 120 may further determine whether the user has specified a percentage, a gain value, or an attenuation value for the sound (e.g., via a selector 235), as discussed above in conjunction with FIG. 3. The processing unit 120 may then block or enhance the sound according to the percentage or value specified by the user.

At step 550, the processing unit 120 determines whether to continue to acquire ambient sound (e.g., via the microphone 110) and process the ambient sound. If the processing unit 120 determines that ambient sound will continue to be acquired and processed, then the method 500 returns to step 510. If the processing unit 120 determines that no additional sound will be acquired and processed, then the method 500 ends.

Figure 6:
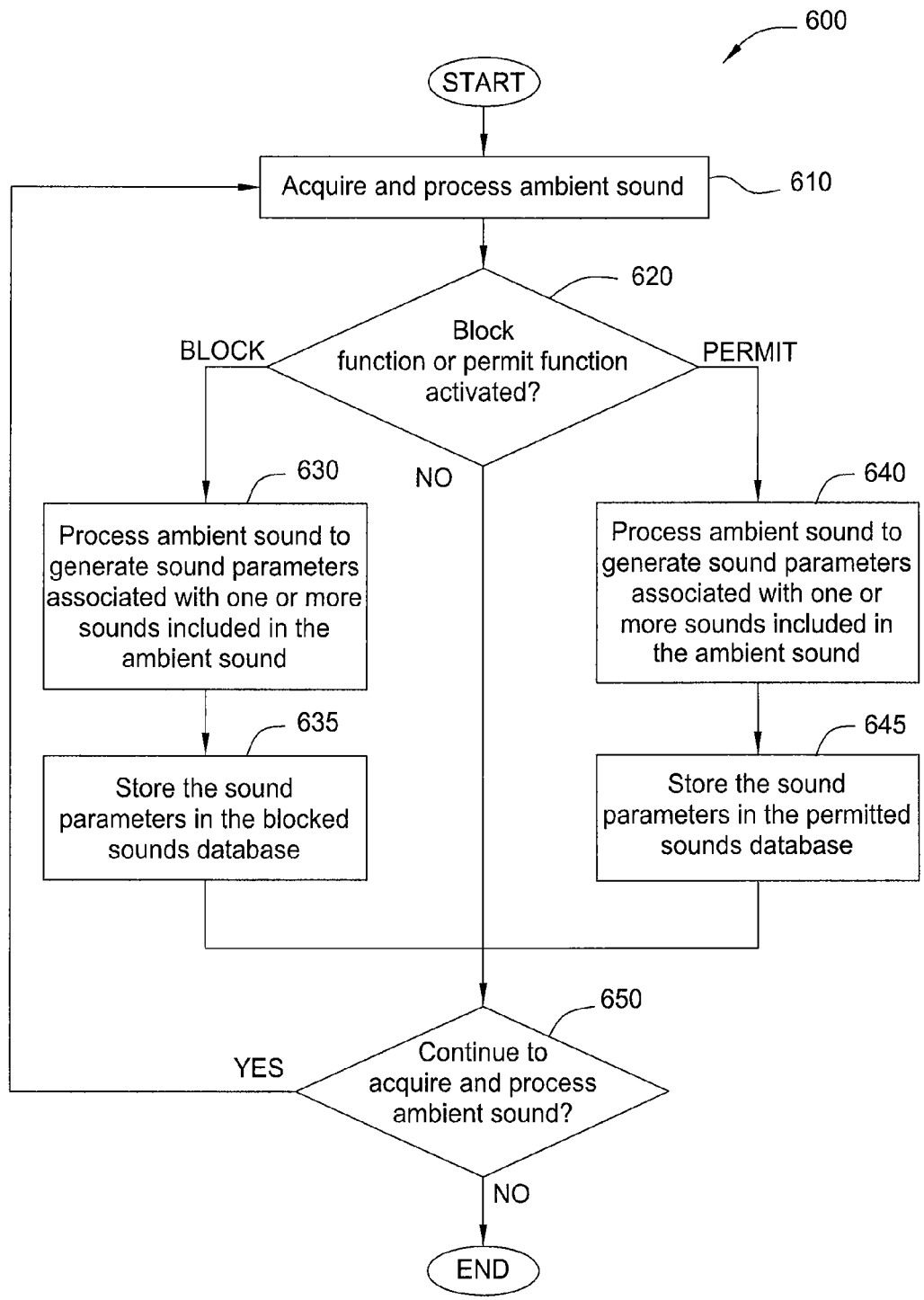
FIG. 6 is a flow diagram of method steps for activating a learning function that determines whether ambient sound is to be blocked, passed, or enhanced by an earplug, according to various embodiments of the present invention.

FIG. 6 is a flow diagram of method steps for activating a learning function that determines whether ambient sound is to be blocked, passed, or enhanced by an earplug, according to various embodiments of the present invention. Although the method steps are described in conjunction with the systems of FIGS. 1A-4, persons skilled in the art will understand that any system configured to perform the method steps, in any order, falls within the scope of the present invention.

As shown, a method 600 begins at step 610, where the microphone 110 acquires ambient sound and transmits signals associated with the ambient sound to the processing unit 120. The processing unit 120 then processes the signals associated with the ambient sound. At step 620, the processing unit 120 determines whether a learning function, such as the block function or the permit function described above, has been activated. If the block function has been activated, then the method 600 proceeds to step 630, where the processing unit 120 processes the ambient sound to generate a set of sound parameters associated with one or more sounds included in the ambient sound. Next, at step 635, the processing unit 120 stores the set of sound parameters in the blocked sounds database. The method 600 then proceeds to step 650.

If the permit function has been activated, then the method 600 proceeds to step 630, where the processing unit 120 processes the ambient sound to generate a set of sound parameters associated with one or more sounds included in the ambient sound. Next, at step 645, the processing unit 120 stores the set of sound parameters in the permitted sounds database. The method 600 then proceeds to step 650.

At step 650, the processing unit 120 determines whether to continue to acquire ambient sound and process the ambient sound. If the processing unit 120 determines that ambient sound will continue to be acquired and processed, then the method 600 returns to step 610. If the processing unit 120 determines that no additional sound will be acquired and processed, then the method 600 ends.

Figure 7:
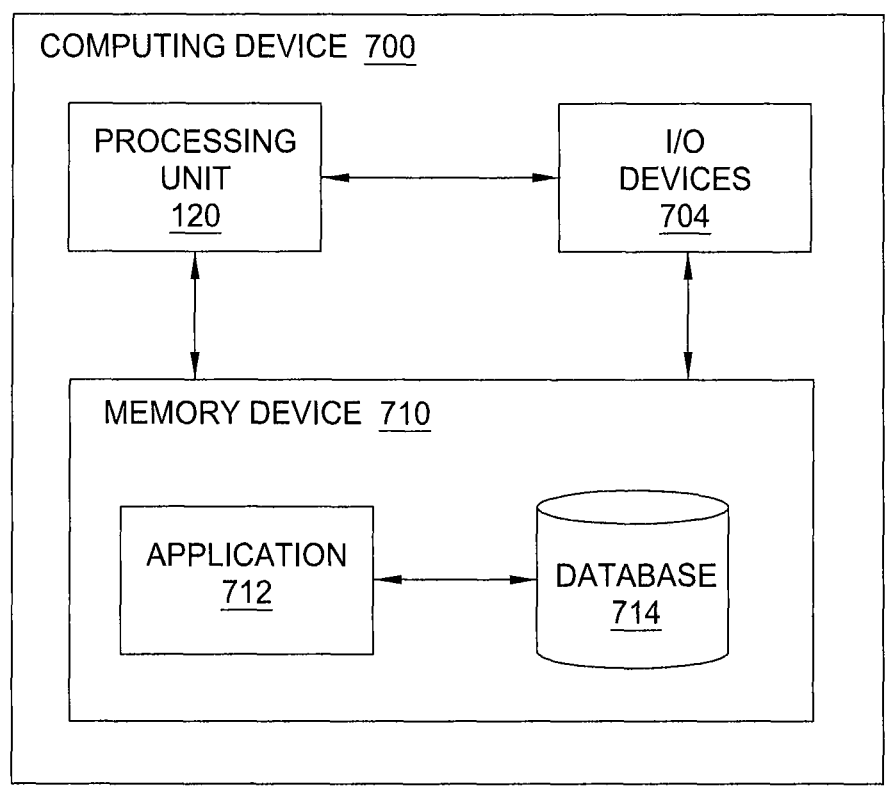
FIG. 7 is a block diagram illustrating a computing device that may be included in the earplug of FIGS. 1A and 1B, according to various embodiments of the present invention.

FIG. 7 is a block diagram illustrating a computing device that may be included in the earplug 100 of FIGS. 1A and 1B, according to various embodiments of the present invention. As shown, computing device 700 includes the processing unit 120, one or more input/output (I/O) devices 704 (e.g., input device 125 and/or wireless module 310), and a memory device 710. Memory device 710 includes an application 712 configured to interact with one or more databases 714 (e.g., a blocked sounds database and/or a permitted sounds database).

Processing unit 120 may include a central processing unit (CPU), digital signal processing unit (DSP), and so forth. I/O devices 704 may include input devices, output devices, and devices capable of both receiving input and providing output. Memory device 710 may include a memory module or collection of memory modules. Software application 712 within memory device 710 may be executed by processing unit 120 to implement the overall functionality of computing device 700, and, thus, to coordinate the operation of the earplug 100 as a whole. The database(s) 714 may store sets of sounds parameters including, for example, frequency ranges and/or digital signatures.

Computing device 700 as a whole may be a microprocessor, an application-specific integrated circuit (ASIC), a system-on-a-chip (SoC), a mobile computing device such as a tablet computer or cell phone, a media player, and so forth. Generally, computing device 700 is configured to coordinate the overall operation of the earplug 100. Any technically feasible system configured to implement the functionality of the earplug 100 falls within the scope of the present invention.

In sum, a microphone included in the earplug acquires ambient sound. The earplug then determines whether one or more sounds included in the ambient sound are associated with sounds parameters stored in the blocked sounds database and/or the permitted sounds database. If a sound included in the ambient sound is associated with sound parameters in the blocked sounds database, then the earplug may generate a cancellation signal associated with the sound. The cancellation signal is then produced for the user to cancel the sound. If a sound included in the ambient sound is associated with sound parameters in the permitted sounds database, then the earplug may pass the sound to the user and/or enhance the sound (e.g., via amplification) for the user. Additionally, the earplug may receive input from the user to activate a sound blocking function and/or a sound permitting function. When the sound blocking function is activated, the earplug acquires ambient sound, generates sound parameters based on the ambient sound, and stores the sound parameters in the blocked sounds database. When the sound permitting function is activated, the earplug acquires ambient sound, generates sound parameters based on the ambient sound, and stores the sound parameters in the permitted sounds database.

One advantage of the techniques described herein is that the user is able to selectively block sounds in the surrounding environment. Additionally, the user is able to specify which sounds are passed through the earplugs and/or enhanced by the earplugs, further increasing the likelihood that the user will not miss useful and/or important sounds in the surrounding environment. Further, the disclosed techniques enable the user to transmit an alarm signal directly to the earplugs such that the user's alarm does not disturb people nearby the user.

One embodiment of the invention may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory devices within a computer such as compact disc read only memory (CD-ROM) disks readable by a CD-ROM drive, flash memory, read only memory (ROM) chips or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored.

The invention has been described above with reference to specific embodiments. Persons of ordinary skill in the art, however, will understand that various modifications and changes may be made thereto without departing from the broader spirit and scope of the invention as set forth in the appended claims. For example, although many of the descriptions herein refer to specific types of sounds that a user may encounter, persons skilled in the art will appreciate that the systems and techniques described herein are applicable to blocking or permitting other types of sounds. The foregoing description and drawings are, accordingly, to be regarded in an illustrative rather than a restrictive sense.

Therefore, the scope of embodiments of the present invention is set forth in the claims that follow.

What is claimed is:

1. An earplug for selectively providing sound to a user, the earplug comprising:
   an earplug body shaped to fit an ear canal of the user and configured to provide noise isolation;
   a microphone disposed in the earplug body and configured to acquire ambient sound;
   a processor disposed in the earplug body and configured to:
      determine that a first sound included in the ambient sound is associated with a first set of sound parameters;
      in response, generate a first cancellation signal associated with the first sound;
      determine that a second sound included in the ambient sound is associated with a second set of sound parameters; and
      in response, generate a second signal to cause the second sound to be produced;
   a speaker disposed in the earplug body and configured to:
      produce one or more sound waves based on the first cancellation signal to cancel the first sound from the ambient sound; and
      produce the second sound based on the second signal; and
   a wireless module that is configured to wirelessly couple to an external computing device and receive the first set of sound parameters and the second set of sound parameters, wherein each of the first set of sound parameters and the second set of sound parameters is individually configured via a plurality of selectors included in a user interface provided by the external computing device.

2. The earplug of claim 1, wherein the second sound acquired by the microphone is associated with a first loudness value, and, in response to determining that the second sound is associated with the second set of sound parameters, the processor is configured to cause the speaker to produce the second sound at a second loudness value that is higher than the first loudness value.

3. The earplug of claim 1, further comprising at least one input device configured to activate a learning function.

4. The earplug of claim 3, wherein the microphone is further configured to acquire a third sound when the learning function is activated by the at least one input device, and the processor is configured to analyze the third sound to generate a third set of sound parameters.

5. The earplug of claim 4, wherein the processor is further configured to:
   determine, based on the third set of sound parameters, that the ambient sound includes the third sound;
   in response, generate a second cancellation signal associated with the third sound; and
   cause the speaker to produce one or more sound waves based on the second cancellation signal to cancel the third sound from the ambient sound.

6. The earplug of claim 4, wherein the processor is further configured to determine, based on the third set of sound parameters, that the ambient sound includes the third sound, and cause the speaker to produce the third sound.

7. The earplug of claim 4, wherein the learning function comprises a block function and a permit function, and the at least one input device comprises a first button configured to activate the block function, and a second button configured to activate the permit function.

8. The earplug of claim 1, further comprising a memory configured to store the first set of sound parameters and the second set of sound parameters.

9. The earplug of claim 1, wherein at least one parameter included in the first set of sound parameters or the second set of sound parameters is associated with a frequency range or a digital sound signature.

10. The earplug of claim 1, wherein a first selector included in the plurality of selectors specifies a first loudness value included in the first set of sound parameters and associated with the first sound, and a second selector included in the plurality of selectors specifies a second loudness value included in the second set of sound parameters and associated with the second sound.

11. The earplug of claim 10, wherein the first loudness value is based on a location of the first selector along a first continuum of sound level values, and the second loudness value is based on a location of the second selector along a second continuum of sound level values.

12. A method for selectively providing sound to a user, comprising:
acquiring ambient sound via a microphone disposed in an earplug body, wherein the earplug body is shaped to fit an ear canal of the user and configured to provide noise isolation from the ambient sound;
determining, via a processor disposed in the earplug body, that a first sound included in the ambient sound is associated with a first set of sound parameters;
in response, generating a first cancellation signal associated with the first sound;
producing, via a speaker disposed in the earplug body, one or more sound waves based on the first cancellation signal to cancel the first sound from the ambient sound;
determining that a second sound included in the ambient sound is associated with a second set of sound parameters;
in response, enhancing the second sound by generating a second signal to cause an enhanced sound to be produced;
producing the enhanced sound based on the second signal; and
receiving the first set of sound parameters and the second set of sound parameters via a wireless module that is configured to wirelessly couple to an external computing device, wherein each of the first set of sound parameters and the second set of sound parameters is individually configured via a plurality of selectors included in a user interface provided by the external computing device.

13. The method of claim 12, wherein the second sound is associated with a first loudness value, and the enhanced sound is associated with a second loudness value that is higher than the first loudness value.

14. The method of claim 12, further comprising:
activating a learning function;
acquiring a third sound when the learning function is activated; and
analyzing the third sound to generate a third set of sound parameters.

15. The method of claim 14, further comprising:
determining, based on the third set of sound parameters, that the ambient sound includes the third sound;
in response, generating a second cancellation signal associated with the third sound; and
producing one or more sound waves based on the second cancellation signal to cancel the third sound from the ambient sound.

16. The method of claim 14, further comprising determining, based on the third set of sound parameters, that the ambient sound includes the third sound, and producing the third sound.

17. The method of claim 14, wherein the learning function comprises a block function and a permit function, and further comprising receiving input via a first button to activate the block function, and receiving input via a second button to activate the permit function.

18. The method of claim 12, further comprising storing the first set of sound parameters and the second set of sound parameters in a local database.

19. The method of claim 12, wherein at least one parameter included in the first set of sound parameters or the second set of sound parameters is associated with a frequency range or a digital sound signature.

20. The method of claim 12, wherein a first selector included in the plurality of selectors specifies a first loudness value included in the first set of sound parameters and associated with the first sound, and a second selector included in the plurality of selectors specifies a second loudness value included in the second set of sound parameters and associated with the second sound.

21. The method of claim 20, wherein the first loudness value is based on a location of the first selector along a first continuum of sound level values, and the second loudness value is based on a location of the second selector along a second continuum of sound level values.

22. A non-transitory computer-readable storage medium including instructions that, when executed by a processor, cause the processor to selectively provide sound to a user, by performing the steps of:
acquiring ambient sound via a microphone disposed in an earplug body, wherein the earplug body is shaped to fit an ear canal of the user and configured to provide noise isolation from the ambient sound;
determining, via a processor disposed in the earplug body, that a first sound included in the ambient sound is associated with a first set of sound parameters;
in response, generating a first cancellation signal associated with the first sound;
producing, via a speaker disposed in the earplug body, one or more sound waves based on the first cancellation signal to cancel the first sound from the ambient sound;
determining that a second sound included in the ambient sound is associated with a second set of sound parameters;
in response, generating a second signal to cause an enhanced sound to be produced, wherein the second sound is associated with a first loudness value that is lower than a second loudness value associated with the enhanced sound;
producing the enhanced sound based on the second signal;
receiving the first set of sound parameters and the second set of sound parameters via a wireless module that is configured to wirelessly couple to an external device, wherein each of the first set of sound parameters and the second set of sound parameters is individually configured via a plurality of selectors included in a user interface provided by the external computing device.

* * * * *